United States Patent [19]

Jacobs et al.

[11] Patent Number: 4,535,096

[45] Date of Patent: Aug. 13, 1985

[54] POLYESTER POLYURETHANE FOAM BASED MEDICAL SUPPORT PAD

[75] Inventors: Barry A. Jacobs, Bethel, Conn.; Gerald Fesman, Teaneck, N.J.

[73] Assignee: Stauffer Chemical Company, Westport, Conn.

[21] Appl. No.: 584,042

[22] Filed: Feb. 27, 1984

[51] Int. Cl.$^3$ .............................................. C08G 18/14
[52] U.S. Cl. ..................................... 521/107; 521/114; 521/128; 521/129; 521/131; 521/132; 521/135
[58] Field of Search ............... 521/107, 114, 128, 129, 521/131, 132, 135

[56] References Cited

U.S. PATENT DOCUMENTS

| | | | |
|---|---|---|---|
| 3,041,293 | 6/1962 | Polacek | 521/107 |
| 3,134,742 | 5/1964 | Wismer et al. | 521/108 |
| 3,135,707 | 6/1964 | Nyquist et al. | 521/106 |
| 3,451,071 | 6/1969 | Whiteley | 5/91 |
| 3,689,948 | 9/1972 | Graves et al. | 5/337 |
| 3,943,077 | 3/1976 | Bell et al. | 252/182 |
| 4,122,049 | 10/1978 | Wagner | 521/136 |
| 4,130,697 | 12/1978 | Stern et al. | 521/106 |
| 4,139,501 | 2/1979 | Rudner et al. | 521/136 |
| 4,251,635 | 2/1981 | Stone | 521/113 |
| 4,264,744 | 4/1981 | Milovanovic et al. | 521/110 |
| 4,275,169 | 6/1981 | Rudner et al. | 521/99 |
| 4,317,889 | 3/1982 | Pcolinsky | 521/107 |
| 4,374,207 | 2/1983 | Stone et al. | 521/107 |
| 4,433,071 | 2/1984 | Fesman | 521/107 |

OTHER PUBLICATIONS

Bruins, *Polyurethane Technology*, Interscience, N.Y. 1969, pp. 52–55.

Frisch et al., (ed), *Advances in Urethane Science & Technology*, Technomic, Westport, CT, 1982, pp. 35–47.

*Chemical Technology: An Encyclopedic Treatment*, Barnes & Noble Books, NY, 1974, pp. 582 & 583.

*Primary Examiner*—Maurice J. Welsh
*Attorney, Agent, or Firm*—Richard P. Fennelly

[57] ABSTRACT

A polyester polyurethane foam formulation useful in medical pads to support bedridden patients is described. The foam is formed by reaction of a polyester polyol, isocyanate and blowing agent combination of water and halogenated hydrocarbon auxiliary blowing agent. A halogenated flame retardant, e.g., an organophosphorus compound, is present. A liquid char forming and dripping ember retardant additive is also present.

28 Claims, No Drawings

POLYESTER POLYURETHANE FOAM BASED MEDICAL SUPPORT PAD

BACKGROUND OF THE INVENTION

Medical support pads, e.g., a foam mattress pad for bedridden patients, must have certain properties. These pads must be sufficiently soft to reduce the formation of bed sores. The pads must have sufficient strength (e.g., tear and tensile) to permit handling, cleaning, and use in an institutional setting without tearing. More recently, these pads must also be flame retardant.

It has been conventional to use a variety of materials in an attempt to develop acceptable medical support pads of this type. For example, U.S. Pat. No. 3,689,948 to D. J. Groves et al. described the use of a polyvinyl alcohol gel support pad. Earlier, U.S. Pat. No. 3,451,071 to J. G. Whiteley described use of a pad containing polyether polyurethane (SEROFOAM brand).

In polyurethane foam technology, the desirable properties of good strength, acceptable softness, and flame retardance are not completely compatible in conventional technology. Polyether polyurethane foams, although usually giving soft and resilient foams, can have such desirable physical properties compromised if high loadings of solid flame retardants are needed. Recent attempts to develop commercial polyether polyurethane foams which might find utility as medical support (or "decubitus") pads have relied upon a higher content of solid filler additives than flame retardant additives. The presence of such solid filler materials cause an unacceptable degradation in the tensile/tear strength of the foam even though the foam is otherwise acceptable in regard to its fire retardance and softness.

SUMMARY OF THE PRESENT INVENTION

The present invention relates to a polyester polyurethane foam; a medical support pad containing it, and to a method of supporting bedridden patients using the support pad. The polyester polyurethane foam is formed by reacting, as essential ingredients, a polyester polyol, isocyanate, water primary blowing agent and halogenated hydrocarbon auxiliary blowing agent, in the presence of a flame retardant amount of a halogenated flame retardant, e.g., an organophosphorus compound, and a char forming and dripping ember retardant additive.

DETAILED DESCRIPTION OF THE PRESENT INVENTION

The general procedure for making the novel polyester polyurethane foam of the invention is practiced by using conventional polyurethane flexible foam forming technology with a novel combination of reactants. Polyurethane foams according to this invention can be prepared by known methods such as the prepolymer, quasi-polymer, or one-shot systems. Foams may be prepared by batch or continuous processes. The foam forming mixture should include as basic ingredients: (A) polyester polyol, (B) organic isocyanate, (C) blowing agent combination (water and, as a critical ingredient, auxiliary halogen-containing blowing agent), (D) optional polyurethane catalyst, (E) optional surfactant, (F) halogenated flame retardant additive, and (G) char forming and dripping ember retardant additive, e.g., water or alcohol soluble urea-formaldehyde resin or a melamine resin.

The polyester polyol ingredient (A) for the polyurethane foam formulation of this invention may be selected from one or a mixture of polyols conventionally used for the preparation of flexible polyester polyurethane foams. Polyester polyols suitable for the preparation of flexible polyurethane foams typically have a molecular weight between 500 and 5000 and hydroxyl numbers of from about 15 to about 300. Suitable polyols include the linear polymeric polyesters prepared from glycols and saturated polycarboxylic acids. For example, difunctional polyester polyols can be prepared by the reaction of diethylene glycol with adipic acid.

The organic isocyanate ingredient (B) of the foam forming process may be selected from conventional isocyanates used for such purposes. Preferably, the isocyanate has an isocyanate functionality of from 2 to 3. Useful isocyanates include the aromatic, aliphatic, cycloaliphatic, and heterocyclic types, and mixtures thereof. Suitable organic isocyanates include toluene diisocyanate and phenylene diisocyanates, with the toluene diisocyanate being preferred because of its cost and availability. The isocyanate can be present at from about 30 to about 50 parts by weight per 100 parts by weight of polyol.

The blowing agent (C) combination comprises water, as the primary blowing agent, in combination with an auxiliary halogenated hydrocarbon blowing agent, such as methylene chloride, or other hydrocarbons or fluorocarbons having a boiling point from about $-30°$ C. to $60°$ C. The use of the auxiliary blowing agent is critical to the present invention. It should be used in amounts ranging from about 8 to about 18 parts by weight of the polyol employed.

The optional polyurethane catalyst ingredient (D) is selected from materials conventional for such purpose. Suitable catalysts include amines such as tertiary amines and metal compounds such as stannous octoate, dibutyltin dilaurate, etc. The catalyst can be present at from about 1 to about 3 parts by weight per 100 parts by weight of polyol.

The optional surfactant ingredient (D) employed in the process of the invention may be selected from surfactants conventionally used for such purposes. Although a variety of surfactants are operative in the process of the invention it has been found that a particularly desirable uniform cell structure and appearance is given to the foam if WITCO M6682 surfactant is used (described as a mixture of fatty acid amides in U.S. Pat. No. 4,317,889). The fatty acid amide type surfactant acts effectively in combination with the halogenated flame retardant additive and water or alcohol soluble urea-formaldehyde resin additives which can be used in the process of the invention. The surfactant can be present at about 1 to about 3 parts by weight per 100 parts by weight of polyol.

The halogenated flame retardant ingredient (F) used in the process and foam of the invention may be selected from conventional polyurethane flame retardant agents of this type. The term, "halogenated flame retardant" as used in the context of this invention includes halogenated hydrocarbons and halogenated organophosphorus compounds. This additive can be present at from about 10 to about 30 parts by weight per 100 parts by weight of polyol.

Examples of suitable halogenated flame retardants are tris(1,3-dichloropropyl)phosphate, tris(2,3-dibromopropyl)phosphate, dichloromethylene-bis(di-2-chloroethyl)phosphate, tris(2-chloroethyl)phosphate, tris(2- chloropropyl)phosphate, 2,2-bis(chloromethyl)-1,3-propylene, bis-di(2-chloroethyl)phosphate, bis(dichloropropyl)tribromoneopentyl phosphate, tetrakis(2-chloroethyl)ethylene diphosphate, oligomeric phosphate esters as described in Canadian Pat. No. 1,127,176, pentabromodiphenyl oxide, bis(pentabromophenoxy)ethane, bis(tetrabromophthalimide)ethane, tetrabromobisphenol A, hexabromocyclododecane, bis(tribromophenoxy)ethane, octabromodiphenyl oxide, tribromoneopentyl alcohol, chlorinated parrafin, brominated paraffin, and mixtures thereof.

The char forming and dripping ember retardant ingredient is preferably a liquid nitrogen-containing compound such as either a urea-formaldehyde resin or a melamine crosslinker resin. Liquid water or alcohol soluble uncrosslinked, i.e., non-thermoset, urea-formaldehyde or urea-formaldehyde derivative precondensate resins which are unreactive, under foam forming conditions, with the organic isocyanate can be used. A representative resin of this type is sold under the trademark BEETLE 65 by American Cyanamid. Also useable as the char forming and dripping ember retardant is a melamine crosslinker, such as a hexa(alkoxyalkyl)melamine resin. Representative additives of this latter type are commercially available. One example is CYMEL 303 resin.

The halogenated flame retardant and the char forming and dripping ember additive are both non-reactive in the polyurethane formulation and their presence does not significantly affect the stoichiometry of the foam forming reaction. The amount of flame retardant and dripping ember retardant additive used in the foam is, preferably, an amount effective to give the combined reduction of flame retardant and dripping ember properties desired by the user. A useful standard for determining suitable levels of additive is the Underwriters' Laboratories UL-94 test. Urethane foam samples passing the HF-1 standard of the UL-94 test are particularly considered to contain effective levels of additive for the purpose of the present invention.

The combined weight of (1) halogenated flame retardant and (2) char forming and dripping ember retardant additive is typically from about 8 to about 20 weight percent of the total weight of the foam formulation ingredients or of the final flexible polyurethane foam product. The ratio of (1) halogenated flame retardant to (2) char forming and dripping ember retardant additive is from about 4:1 to about 1:1, with a ratio range of from 3:1 to 2:1 being preferred.

The desired level of flame retardance is principally achieved by the amount and type of flame retardant and char forming/dripping retardant additive. The presence of auxiliary blowing agent is principally responsible for the desired degree of softness achieved as compared to a conventional polyester polyurethane foam which utilizes only water as a blowing agent (as exemplified in U.S. Pat. Nos. 4,139,501, 4,251,635, 4,275,169, and 4,317,889). The desired degree of tensile tear strength is principally due to the inherent nature of the polyester polyurethane foam which has been selected for use in regard to the present invention.

The interaction between the various ingredients used in making the foams of the present invention are complex. The desired degree of flame retardance, softness, and tensile tear strength in the foams of the present invention can be achieved by selecting the following approximate amounts for the halogenated flame retardant, char former/dripping ember retardant additive, and auxiliary blowing agent (all parts per weight being based on 100 parts by weight of polyester polyol):

| Ingredient | Broad Range | Preferred Range |
| --- | --- | --- |
| Halogenated flame retardant | 5-30 | 10-20 |
| Char former/dripping ember retardant | 2-25 | 5-15 |
| Auxiliary blowing agent | 3-25 | 5-15 |

Representative foams made in accordance with the present invention have the following preferred physical characteristics:

| Characteristic | Value |
| --- | --- |
| Flame retardance[1] | $\leq 3.175$ cm. burned |
| Softness (50% CLD)[2] | 25-50 gm/cm$^2$ |
| Tear Strength[3] | 0.30-0.60 kg/1. cm. |
| Tensile Strength[4] | 750-1500 gm cm$^2$ |
| Elongation[5] | 80%-200% |

[1] by UL-94 HFl test method.
[2] by ASTM 3564 - Compression Load Deflection (CLD).
[3] by ASTM 3564, Test F.
[4] by ASTM 3564, Test E.
[5] by ASTM 3564, Test E.

Certain embodiments of the present invention are set forth in the Examples which follow.

TEST METHOD FOR FLAME RETARDANCY

The urethane foams described in the Examples which follow were placed on an asbestos/cement board (50.8 cm.$\times$50.8 gm.) covered with aluminum foil. The foam was then covered with two sheets (50.8 cm.$\times$50.8 cm.) made of 50/50 cotton-polyester sheeting material. The cover sheet was then folded over and the sample was ignited in front of the fold with a methenamine pill.

Specimens 38.1 cm.$\times$38.1 cm.$\times$3.81 cm. in dimension (non-convoluted) were tested in Examples 1-7 and 8 (Nos. 1 and 2).

Convoluted specimens (30.5 cm.$\times$30.5 cm.$\times$3.81 cm.) were tested in Example 8 (Nos. 3, 4 and 5).

DESCRIPTION OF INGREDIENTS USED IN URETHANE FORMULATIONS

FOMREX 53 Polyol (Witco Chemical Co.): A polyester polyol made from adipic acid and diethylene glycol, with a small percentage of a trihydric alcohol, such as glycerol. The molecular weight can range from 900-5000, preferably about 2000, with an OH number of 45-60 mg. KOH/gm.

WITCO 7786: a sulfated of sulfonated fatty acid ester based on polyoxyethylated fatty acid. It serves as a surfactant.

WITCO 1058: diethylammonium oleate; which also serves as a surfactant.

Nem: N-ethylmorpholine, which serves as a catalyst

DM16D: hexadecyl dimethylamine having the formula $(CH_3)_2NC_{16}H_{33}$. It serves as a catalyst.

TDI: toluene diisocyanate (80% - 2,4 isomer and 20%-2,6 isomer) to react with the polyol and form urethane linkages.

FYROL FR-2: tri(beta,beta'-dichloroisopropyl)phosphate flame retardant from Stauffer Chemical Company.

CYMEL 303: Hexa(methoxymethyl)melamine crosslinker, a char former and dripping agent retardant additive.

ISOTRON 11-B: Trichlorofluoromethane auxiliary blowing agent.

IXOL-B 251: halogenated polyether polyol (from Solvay) which is derived from epichlorohydrin and a brominated polyol.

BEETLE 65: methylated urea-formaldehyde resin from American Cyanamid, a char former and dripping ember retardant additive.

L-532: silicone organo-modified copolymer surfactant for polyester urethane foams (from Union Carbide).

L-536: silicone surfactant for flame retarded polyester urethane foams (from Union Carbide).

M66-82A: organic surfactant for polyester urethane foams (from Witco Chemical).

AEROTEX 3030: hexa(methoxymethyl)melamine crosslinker (from American Cyanamid), a char former and dripping ember retardant additive.

DESCRIPTION OF PROCEDURE USED TO MAKE FLEXIBLE POLYESTER FOAM

A premix solution of water (3.6 parts per 100 parts of polyol), WITCO 7786 surfactant (1.4 php), WITCO 1058 surfactant (1.4 php), Nem (1.9 php) and DM16D catalyst (0.3 php) was prepared. FOMREZ 53 brand polyol was poured into a mixing cup and any desired flame retardant and blowing agent was added. The mixture was pre-mixed for 25 seconds, water was added, and the mixture was mixed again for 25 seconds. Pre-weighed TDI-80/20 was poured into the mixture, and the resulting mixture was mixed for 8 seconds and poured into a cake box. After the foam had risen, it was heated at 120° C. in an oven for 15 minutes to cure.

EXAMPLE 1

This Example illustrates formation of three polyester polyurethane foam formulations containing hexamethoxy methylmelamine crosslinker.

| Ingredient | Formulation No. | | |
|---|---|---|---|
| | 1* | 2 | 3 |
| FOMREZ 53 polyol | 100 | 100 | 100 |
| WITCO 7786 | 1.4 | 1.4 | 1.4 |
| WITCO 1058 | 1.3 | 1.3 | 1.3 |
| Nem | 1.9 | 1.9 | 1.9 |
| DM16D | 0.3 | 0.3 | 0.3 |
| Water | 3.6 | 3.6 | 3.6 |
| TDI | 44.0 | 44.0 | 44.0 |
| FYROL FR-2 | 11.25 | 11.25 | 11.25 |
| CYMEL 303 | 3.75 | 3.75 | 3.75 |
| ISOTRON 11-B | — | 5 | — |
| CH$_2$Cl$_2$ | — | — | 5 |
| Burn Time | 18 min. | 21 min. | 23 min. |

*not part of the present invention.

In all three cases the sheet material burned but a minimal amount of foam was consumed. Foam formulations 2 and 3 were both softer than formulation 1. The flammability of formulations 2 and 3 was not unduly harmed by presence of the auxiliary blowing agents (CH$_2$Cl$_2$ and ISOTRON 11-B brand).

EXAMPLE 2

This Example illustrates an attempt to make an even softer foam than any shown in Example 1 by raising the level of trichlorofluoromethane blowing agent (ISOTRON 11-B brand).

| Ingredient | Formulation No. | |
|---|---|---|
| | 1 | 2* |
| FOMREZ 53 | 100 | 100 |
| WITCO 7786 | 1.4 | 1.4 |
| WITCO 1058 | .1.3 | 1.3 |
| Nem | 1.9 | 1.9 |
| DM16D | 0.3 | 0.3 |
| Water | 3,6 | 3.6 |
| TDI | 44.0 | 44.0 |
| FYROL FR-2 | 11.25 | 12.0 |
| CYMEL 303 | 3.75 | — |
| ISOTRON 11-B | 10 | 10 |
| Burn Time | 26 min. | 12 min. |

*not part of the present invention.

Approximately one-third of Foam No. 1 was thoroughly consumed during the burn test, whereas Foam No. 2 was entirely consumed. The Example illustrates the superior results obtained when CYMEL 303 char former is present in No. 1 as compared to No. 2.

EXAMPLE 3

This Example illustrates attempts to increase the level of flame retardant and crosslinking agent and include a bromine-containing polyether polyol (IXOL-B 251) to achieve some increased degree of crosslinking to improve the flame retardancy of the foam.

| Ingredient | 1* | 2* | 3* | 4* | 5 |
|---|---|---|---|---|---|
| FOMREZ 53 | 100 | 100 | 100 | 100 | 100 |
| WITCO 7786 | 1.4 | 1.4 | 1.4 | 1.4 | 1.4 |
| WITCO 1058 | 1.3 | 1.3 | 1.3 | 1.3 | 1.3 |
| Nem | 1.9 | 1.9 | 1.9 | 1.9 | 1.9 |
| DM16D | 0.3 | 0.3 | 0.3 | 0.3 | 0.3 |
| Water | 3.6 | 3.6 | 3.6 | 3.6 | 3.6 |
| TDI | 44.0 | 44.0 | 44.0 | 44.0 | 44.0 |
| FYROL FR-2 | 20 | — | 15 | 15 | 20 |
| FYROL 2XC20 | — | 25 | — | — | — |
| CYMEL 303 | 5 | — | — | — | 5 |
| IXOL B 251 | — | — | 10 | 10 | — |
| ISOTRON 11-B | — | 10 | — | 10 | 10 |
| Burn Time | None | 17 min. | 16 min. | 17 min. | 21 min. |

*not part of the present invention.

All foams were observed to have small holes in their surface believed due to a longer premix time (2 min.) than optimum.

Foam No. 1 did not burn, but was not of the desired softness due to the absence of auxiliary blowing agent.

Foam No. 2 burned for 17 minutes and failed the test since it was consumed entirely. It contained no char former/dripping ember additive.

Foam No. 3 burned 16 minutes and passed the test since it formed a dry char. It was not of the desired softness.

Foam No. 4 burned 17 min. with a yellowish gas (possibly chlorine or bromine) being observed. It failed the test since about 95% of the foam was consumed. It was a relatively soft foam.

Foam No. 5 burned 21 minutes, formed a dry char thereby passing the test and was a soft foam similar in softness to Foam No. 4. It had a far superior burn time as compared to Foam Nos. 1–4.

Selected physical properties for Foam Nos. 3 and 5 are given in Example 7.

EXAMPLE 4

In this Example polyester polyurethane foams are made using an increased level of hexamethoxy methylmelamine crosslinker compared to the foams in preceding Examples.

| Ingredient | Formulation No. 1* | 2 |
|---|---|---|
| FOMREZ 53 | 100 | 100 |
| WITCO 7786 | 1.4 | 1.4 |
| WITCO 1058 | 1.3 | 1.3 |
| Nem | 1.9 | 1.9 |
| DM16D | 0.3 | 0.3 |
| Water | 3.6 | 3.6 |
| TDI | 44.0 | 44.0 |
| CYMEL 303 | 10 | 10 |
| FYROL FR-2 | 20 | — |
| FYROL 2XC20 | — | 20 |
| ISOTRON B-11 | — | 10 |
| Burn Time | 15 min. | 21 min. |

*not part of the present invention.

In this Example the formulation for Foam No. 1 had only been premixed 1 minute. The toluene diisocyanate was added 10 seconds thereafter.

Foam No. 1 passed the burn test but was relatively stiffer than Foam No. 2.

Foam No. 2 burned 21 minutes with make-up air (14 minutes without make-up air) and passed the burn test. No difference in the consumption of the foam was noted either with or without make-up air.

Both foams were judged acceptable in regard to their flame retardancy.

COMPARATIVE EXAMPLE 5

This Example illustrates fabrication of softer polyester urethane foams for purposes of greater ease in the fabrication of convoluted decubitus pads.

| Ingredient | Formulation No. | | | |
|---|---|---|---|---|
| | 1 | 2 | 3 | 4 |
| FOMREZ 53 | 100 | 100 | 100 | 100 |
| WITCO 7786 | 1.4 | 1.4 | 1.4 | 1.4 |
| WITCO 1058 | 1.3 | 1.3 | 1.3 | 1.3 |
| Nem | 1.9 | 1.9 | 1.9 | 1.9 |
| DM16D | 0.3 | 0.3 | 0.3 | 0.3 |
| Water | 3.6 | 3.6 | 3.6 | 3.6 |
| TDI | 44.0 | 44.0 | 44.0 | 44.0 |
| FYROL FR-2 | — | — | — | 20 |
| FYROL 2XC20 | 20 | 20 | 20 | — |
| CYMEL 303 | 15 | 10 | 10 | 10 |
| ISOTRON 11-B | 20 | 15 | 12 | 12 |
| Burn Time (Min.) | 6 | — | — | — |
| % wt. loss | 35 | — | — | — |

Very large cells were formed in Foam No. 1 believed to be due to the levels of ISOTRON 11-B brand material used. It was used at 20 phr rather than 10 phr as in Example 4, No. 2.

Foam Nos. 2–4 were not burned due to similar large cell formation using somewhat lesser amounts of ISOTRON 11-B. Better cell structure control was later obtained (see Example 6) by preblending the fluorocarbon auxiliary blowing agent with the polyol and also by incorporation of surfactant (M66-82A) into the formulation.

EXAMPLE 6

This Example illustrates synthesis of polyester urethane foams and gives the weight loss after the burn test. Foam Nos. 2, 4 and 5 had a convoluted upper surface whereas Foams 1 and 3 had a non-convoluted surface.

| Ingredient | Formulation No. | | | |
|---|---|---|---|---|
| | 1 | 2 | 3 | 4 |
| FOMREZ 53 | 100 | 100 | 100 | 100 |
| M66-82A | 1.0 | — | — | 1.0 |
| WITCO 1058 | 1.3 | 1.3 | 1.3 | 1.3 |
| WITCO 7786 | — | 1.4 | 1.4 | — |
| Nem | 1.9 | 1.9 | 2.5 | 2.2 |
| DM16D | 0.3 | 0.3 | 0.5 | 0.5 |
| Water | 3.6 | 3.6 | 3.6 | 3.6 |
| TDI | 44.0 | 44.0 | 44.0 | 44.0 |
| FYROL FR-2 | 20 | 20 | 20 | 20 |
| BEETLE 65 | 10 | — | — | 10 |
| ISOTRON 11-B | 10 | 14 | 14 | 10 |
| Aluminum Trihydrate | — | 20 | 20 | — |
| AEROTEX 3030 | — | — | 10 | — |
| Burn Time (Min.) | 20 | — | — | — |
| % wt. loss | 9.3 | 73.7 | 4 | 26.6 |

These data illustrate that Sample 1 (non-convoluted) had a lower weight loss than Sample 4 (convoluted).

EXAMPLE 7

This Example sets forth the respective physical properties for various flexible polyurethane foams.

| Test | CHMR[1] Foam | Ex. 3[2] No. 3 | Ex. 3[3] No. 5 | Polyether[4] Foam |
|---|---|---|---|---|
| Density (kg/m$^3$) | 83.13 | 41.17 | 28.67 | 28.51 |
| Air Flow (cc/sec) | 1038.4 | 188.8 | 2548.8 | 1416 |
| 50% compression Force (g/cm$^2$) | 59.76 | 65.39 | 29.53 | 42.18 |
| Tensile Str. at Break (g/cm$^2$) | 625.7 | 1490.5 | 1061.6 | 1040.5 |
| Elongation at Break (%) | 77 | 165 | 190 | 190 |
| Tear Str. (kg/1. cm) | 0.18 | 0.59 | 0.54 | 0.61 |

[1] CHMR Foam = combustion modified high resilient foam. It is formed from the formulation described below.
[2] not part of the present invention since it is a polyester foam formed without auxiliary blowing agent.
[3] part of the present invention.
[4] a polyether foam formed from the formulation described below.
CHMR Foam Formulation: Polyether polyol (MULTRANOL E-9238 brand) - 100 parts by weight (pbw); hydrated alumina (SOLEM 136 5B brand) - 120 pbw; antimony oxide - 8 pbw; decabromodiphenyl oxide (SAYTEX 102 brand) - 22 pbw; ethyl maleic anhydride - 5 pbw; water - 2 pbw; silicone surfactant (UCC Y10223 brand - 2 pbw; diethanolamine (15 wt %) - 1.8 pbw; tertiary amine catalyst (POLYCAT 77-50 brand) - 0.4 pbw; tin catalyst (M and T T-12 brand) - 0.8 pbw; amine catalyst (DABCO 33LV brand) - 0.1 pbw; trichlorofluoromethane (ISOTRON 11B brand) - 7 pwb; chlorinated phosphate flame retardant (FYROL FR-2 brand) - 30 pbw; and toluene diisocyanate (MONDUR TD-80 brand) - 33.5 pbw.
Polyether foam formulation: Polyether polyol (UCC 1656 brand) - 100 pbw; surfactant (UCC L5740 brand) - 1.4 pbw; n-ethylmorpholine - 1.3 pbw; tin catalyst (M and T T-10 brand) - 0.42 pbw; CH$_2$Cl$_2$ - 1.5 pbw; water - 3.85 pbw; and toluene diisocyanate (MONDUR TD-80 brand) - 51.22 pbw. Toluene diisocyanate index: 111.

The polyurethane foams of the present invention are useful as medical pads to support bedridden patients. In a preferred embodiment, the medical pad consists of the foam without any other material forming a cover for the foam. In such a pad, the bottom surface is flat and the upper surface (designed to support the patient) has a plurality of raised, generally conical protrusions. Such a design, when placed below a suitable bed sheet, allows for support of the patient by the protrusions without the formation of decubitus ulcers or bedsores.

The foregoing Examples are merely intended to describe certain embodiments of the present invention and, for this reason, should not be construed in a limiting sense. The scope of protection that is sought is set forth in the claims which follow.

What is claimed:

1. A polyurethane foam adapted to be used as a medical support pad material for bedridden patients which is formed by the reaction of a polyester polyol, isocyanate, and blowing agent combination of water and halogenated hydrocarbon auxiliary blowing agent and which contains an effective flame retardant amount of halogenated flame retardant and a char forming and dripping ember retardant additive.

2. A foam as claimed in claim 1 wherein the flame retardant is an organophosphorus compound.

3. A foam as claimed in claim 1 wherein the char forming and dripping ember retardant additive is a liquid nitrogen containing resin.

4. A foam as claimed in claim 1 wherein the halogenated flame retardant comprises from about 5 to about 30 parts by weight per 100 parts by weight of polyol, the char forming and dripping ember retardant additive comprises from about 2 to about 25 parts by weight per 100 parts by weight of polyol and the auxiliary blowing agent comprises from about 3 to about 25 parts by weight of polyol.

5. A foam as claimed in claim 1 wherein the halogenated flame retardant comprises from about 10 to about 20 parts by weight per 100 parts by weight of polyol, the char forming and dripping ember retardant additive comprises from about 5 to about 15 parts by weight per 100 parts by weight of polyol and the auxiliary blowing agent comprises from about 5 to about 15 parts by weight of polyol.

6. A foam as claimed in claim 4 wherein the halogenated flame retardant is an organophosphorus flame retardant, the char forming and dripping ember retardant additive is a liquid nitrogen-containing compound and the auxiliary blowing agent is a halogenated hydrocarbon blowing agent.

7. A foam as claimed in claim 5 wherein the halogenated flame retardant is an organophosphorus flame retardant, the char forming and dripping ember retardant additive is a liquid urea-formaldehyde resin and the auxiliary blowing agent is a halogenated hydrocarbon blowing agent.

8. A foam formulation as claimed in claim 5 wherein the halogenated flame retardant is an organophosphorus flame retardant, the char forming and dripping ember retardant additive is a liquid melamine crosslinking resin and the auxiliary blowing agent is a halogenated hydrocarbon blowing agent.

9. A polyester polyurethane foam adapted to be used as a medical support pad for bedridden patients which contains an effective flame retardant amount of halogenated flame retardant and a char forming and dripping ember retardant additive and which has a 50% compression load deflection of from about 25–50 gm/cm$^2$.

10. A foam as claimed in claim 9 wherein the flame retardance is less than or equal to about 3.175 cm. burned when tested in accordance with UL-94 HF1 test method.

11. A foam as claimed in claim 10 wherein the tear strength is from about 0.30 to about 0.60 lg/l.cm.

12. A medical support pad comprising the foam of claim 1.

13. A medical support pad comprising the foam of claim 4.

14. A medical support pad comprising the foam of claim 5.

15. A medical support pad comprising the foam of claim 7.

16. A medical support pad comprising the foam of claim 8.

17. A medical support pad comprising the foam of claim 9.

18. A medical support pad comprising the foam of claim 10.

19. A medical support pad comprising the foam of claim 11.

20. A medical support pad, having a substantially flat bottom surface with a convoluted upper surface comprising a plurality of raised, generally conical protrusions, which consists of the foam of claim 1.

21. A medical support pad, having a substantially flat bottom surface with a convoluted upper surface comprising a plurality of raised, generally conical protrusions, which consists of the foam of claim 4.

22. A medical support pad, having a substantially flat bottom surface with a convoluted upper surface comprising a plurality of raised, generally conical protrusions, which consists of the foam of claim 5.

23. A medical support pad, having a substantially flat bottom surface with a convoluted upper surface comprising a plurality of raised, generally conical protrusions, which consists of the foam of claim 6.

24. A medical support pad, having a substantially flat bottom surface with a convoluted upper surface comprising a plurality of raised, generally conical protrusions, which consists of the foam of claim 7.

25. A medical support pad, having a substantially flat bottom surface with a convoluted upper surface comprising a plurality of raised, generally conical protrusions, which consists of the foam of claim 8.

26. A medical support pad, having a substantially flat bottom surface with a convoluted upper surface comprising a plurality of raised, generally conical protrusions, which consists of the foam of claim 9.

27. A medical support pad, having a substantially flat bottom surface with a convoluted upper surface comprising a plurality of raised, generally conical protrusions, which consists of the foam of claim 10.

28. A medical support pad, having a substantially flat bottom surface with a convoluted upper surface comprising a plurality of raised, generally conical protrusions, which consists of the foam of claim 10.

* * * * *

UNITED STATES PATENT AND TRADEMARK OFFICE
CERTIFICATE OF CORRECTION

PATENT NO. : 4,535,096
DATED : August 13, 1985
INVENTOR(S) : Barry A. Jacobs and Gerald Fesman It is certified that error appears in the above—identified patent and that said Letters Patent is hereby corrected as shown below:

Col. 4, line 46, "FOMREX 53" should read -- FOMREZ 53 --;

Col. 6, line 7, under Formulation No. 1, the value for the WITCO 1058 material should read -- 1.3 -- rather than ".1.3";

Col. 6, line 8, under Formulation No. 1, the value for the water should read -- 3.6 -- rather than "3,6";

Col. 8, line 47, "pwb" should read -- pbw --; and

Col. 10, line 56, the dependency of Claim 28 should be changed to -- Claim 11 -- from "Claim 10".

Signed and Sealed this

Tenth Day of December 1985

[SEAL]

Attest:

DONALD J. QUIGG

Attesting Officer

Commissioner of Patents and Trademarks